US012588886B2

(12) United States Patent
Peng et al.

(10) Patent No.: US 12,588,886 B2
(45) Date of Patent: Mar. 31, 2026

(54) METHOD AND APPARATUS FOR DETERMINING TOUCH PANEL TO OBJECT DISTANCE IN X-RAY IMAGING

(71) Applicant: Siemens Shanghai Medical Equipment Ltd., Shanghai (CN)

(72) Inventors: Xi Shuai Peng, Shanghai (CN); Jing Tai Cao, Shanghai (CN); Yun Zhe Zou, Shanghai (CN)

(73) Assignee: Siemens Shanghai Medical Equipment Ltd., Shanghai (CN)

( * ) Notice: Subject to any disclaimer, the term of this patent is extended or adjusted under 35 U.S.C. 154(b) by 150 days.

(21) Appl. No.: 18/685,035

(22) PCT Filed: Aug. 24, 2021

(86) PCT No.: PCT/CN2021/114385
§ 371 (c)(1),
(2) Date: Feb. 20, 2024

(87) PCT Pub. No.: WO2023/023955
PCT Pub. Date: Mar. 2, 2023

(65) Prior Publication Data
US 2024/0215942 A1     Jul. 4, 2024

(51) Int. Cl.
*A61B 6/00* (2024.01)
*A61B 6/58* (2024.01)

(52) U.S. Cl.
CPC ............ *A61B 6/589* (2013.01); *A61B 6/5258* (2013.01); *A61B 6/547* (2013.01); *A61B 6/588* (2013.01)

(58) Field of Classification Search
None
See application file for complete search history.

(56) References Cited

U.S. PATENT DOCUMENTS

| 7,796,724 | B2 | 9/2010 | Ito |
| 2010/0074404 | A1 | 3/2010 | Ito |
| 2023/0263498 | A1* | 8/2023 | Slagmolen ................ G06T 7/73 |
| | | | 378/207 |

FOREIGN PATENT DOCUMENTS

| CN | 111000576 A | 4/2020 |
| JP | 2007064906 A | 3/2007 |

OTHER PUBLICATIONS

Feb. 14, 2022 (PCT) International Search Report and Written Opinion—App. PCT/CN2021/114385.

* cited by examiner

*Primary Examiner* — Hoon K Song
(74) *Attorney, Agent, or Firm* — Banner & Witcoff, Ltd.

(57) ABSTRACT

The present disclosure is directed to a method and apparatus for determining a touch panel to object distance (TOD) in X-ray imaging. This includes obtaining a three-dimensional image of a to-be-detected subject that includes an object; determining a source to image distance (SID) and a touch panel to detector distance (TDD); determining, based on the three-dimensional image, a distance between a light source of a camera assembly that captures the three-dimensional image and a predetermined key point located on a surface of the to-be-detected subject, where the predetermined key point corresponds to an X-ray imaging protocol; and determining the TOD based on the SID, the TDD, and the distance between the light source and the predetermined key point. The implementations of the present disclosure implement automatic measurement of a TOD, reduce the complexity, and further improve the accuracy of the TOD.

13 Claims, 7 Drawing Sheets

METHOD AND APPARATUS FOR DETERMINING TOUCH PANEL TO OBJECT DISTANCE IN X-RAY IMAGING

CROSS-REFERENCE TO RELATED APPLICATIONS

The present application is a U.S. National Stage entry of PCT Application no. PCT/CN2021/114385, filed Aug. 24, 2021, the contents of which are incorporated herein by reference in its entirety.

TECHNICAL FIELD

The present disclosure relates to the field of medical imaging technologies, and in particular, to a method and apparatus for determining a touch panel to object distance (TOD) in X-ray imaging.

BACKGROUND

X-rays are electromagnetic radiation with a wavelength between ultraviolet light and gamma rays. X-rays are penetrative and have different penetrating capacities for substances of different densities. In medicine, X-rays are generally used to project human organs and bones to form medical images.

An X-ray imaging system generally includes an X-ray generation assembly, a Bucky wall stand (BWS) assembly, an examination table assembly, a film holder assembly including a flat panel detector, a remote control host, and the like. The X-ray generation assembly emits, by using a high voltage provided by a high-voltage generator, X-rays that penetrate an irradiated imaging target, and forms medical image information of the imaging target on the flat panel detector. The flat panel detector sends the medical image information to the control host. The imaging target may stand near the BWS assembly or lie on the examination table assembly, so as to receive X-ray photography of parts such as the head, chest, abdomen, and joints.

In an X-ray application program, a distance between a touch panel touched by a to-be-detected subject including an object and the object generally needs to be determined. For example, the object may be tissue, an organ, or a system of the to-be-detected subject. The TOD not only affects the quality of an X-ray image, but may also affect a dose. For example, in an application such as long bone splicing or free-mode dose control, a TOD indicator is particularly critical.

In a current practical application, a TOD is generally manually measured by staff using a ruler. However, under natural conditions, it is difficult for the staff to observe objects (such as the spine and the femur) inside a to-be-detected subject. Therefore, manually measuring the TOD is not only cumbersome and time-consuming, but also has deviations.

SUMMARY

Implementations of the present disclosure provide a method and apparatus for determining a TOD in X-ray imaging.

The technical solutions of the implementations of the present disclosure include the following:

A method for determining a TOD in X-ray imaging is provided, including:

obtaining a three-dimensional image of a to-be-detected subject that includes an object;

determining a source to image distance (SID) and a touch panel to detector distance (TDD);

determining, based on the three-dimensional image, a distance between a light source of a camera assembly that captures the three-dimensional image and a predetermined key point located on a surface of the to-be-detected subject, where the predetermined key point corresponds to an X-ray imaging protocol; and determining the TOD based on the SID, the TDD, and the distance between the light source and the predetermined key point.

It can be seen that, in this implementation of the present disclosure, the TOD can be automatically determined based on the three-dimensional image of the to-be-detected subject without manual measurement, thereby reducing the complexity.

In an implementation, the determining, based on the three-dimensional image, a distance between a light source and a predetermined key point located on a surface of the to-be-detected subject includes:

inputting the three-dimensional image into a key point recognition network;

enabling the key point recognition network to recognize the predetermined key point located on the surface of the to-be-detected subject in the three-dimensional image; and determining, based on a distance measurement algorithm, the distance between the light source and the recognized predetermined key point.

Therefore, in this implementation of the present disclosure, the processing efficiency can be greatly improved by recognizing the predetermined key point through artificial intelligence.

In an implementation, an X-ray source coincides with the light source; and the determining the TOD based on the SID, the TDD, and the distance between the light source and the predetermined key point includes:

determining the TOD, where TOD=γ*(SID−TDD−SOSD1), where

SID represents the source to image distance, TDD represents the touch panel to detector distance, SOSD1 represents the distance between the light source and the predetermined key point, and γ represents a correction factor.

It can be seen that when the X-ray source coincides with the light source of the camera assembly that captures the three-dimensional image, the TOD is calculated in this implementation of the present disclosure. In addition, the correction factor is introduced, thereby improving the calculation precision.

In an implementation, an X-ray source does not coincide with the light source; and the determining the TOD based on the SID, the TDD, and the distance between the light source and the predetermined key point includes:

determining a distance SOSD1 between the X-ray source and the predetermined key point based on the distance SOSD2 between the light source of the camera assembly and the predetermined key point; and determining the TOD, where TOD=γ*(SID−TDD−SOSD1), SID represents the source to image distance, TDD represents the touch panel to detector distance, and γ represents a correction factor.

It can be seen that when the X-ray source does not coincide with the light source of the camera assembly that captures the three-dimensional image, the TOD can be also calculated in this implementation of the present disclosure. In addition, the correction factor is introduced, thereby improving the calculation precision.

In an implementation, the determining a distance SOSD1 between the X-ray source and the predetermined key point based on the distance SOSD2 between the light source of the camera assembly and the predetermined key point includes:

determining a transformation matrix from a coordinate system of the camera assembly to a coordinate system of an X-ray generation assembly;

determining three-dimensional coordinates of the predetermined key point in the coordinate system of the camera assembly based on the distance SOSD2 between the light source and the predetermined key point;

determining three-dimensional coordinates of the predetermined key point in the coordinate system of the X-ray generation assembly based on the three-dimensional coordinates of the predetermined key point in the coordinate system of the camera assembly and the transformation matrix; and determining the distance SOSD1 between the X-ray source and the predetermined key point based on the three-dimensional coordinates of the predetermined key point in the coordinate system of the X-ray generation assembly.

Therefore, in this implementation of the present disclosure, the distance between the X-ray source and the predetermined key point can be conveniently determined through coordinate transformation.

In an implementation, the method further includes:

inputting the three-dimensional image into a correction factor determining network corresponding to the X-ray imaging protocol, to determine the correction factor by the correction factor determining network; or determining the correction factor based on a user input.

It can be seen that, in this implementation of the present disclosure, the correction factor can be determined in various manners, and in particular, the correction factor can be determined through artificial intelligence, thereby reducing the dependence on user experience.

In an implementation, the method further includes:

labeling respective correction factors for historical three-dimensional images as training data; and training a neural network model by using the labeled historical three-dimensional images, where when an accuracy rate of an output result of the neural network model is greater than a predetermined threshold, the correction factor determining network is obtained.

Therefore, a training process for the correction factor determining network is further implemented based on the training data in this implementation of the present disclosure.

An apparatus for determining a TOD in X-ray imaging is provided, including:

an obtaining module, configured to obtain a three-dimensional image of a to-be-detected subject that includes an object;

a first determining module configured to determine a SID and a TDD;

a second determining module configured to determine, based on the three-dimensional image, a distance between a light source of a camera assembly that captures the three-dimensional image and a predetermined key point located on a surface of the to-be-detected subject, where the predetermined key point corresponds to an X-ray imaging protocol; and a third determining module configured to determine the TOD based on the SID, the TDD, and the distance between the light source and the predetermined key point.

It can be seen that in this implementation of the present disclosure, the TOD can be automatically determined based on the three-dimensional image of the to-be-detected subject without manual measurement, thereby reducing the complexity.

In an implementation, the second determining module is configured to input the three-dimensional image into a key point recognition network; enable the key point recognition network to recognize the predetermined key point located on the surface of the to-be-detected subject in the three-dimensional image; and determine, based on a distance measurement algorithm, the distance between the light source and the recognized predetermined key point.

Therefore, in this implementation of the present disclosure, the processing efficiency can be greatly improved by recognizing the predetermined key point through artificial intelligence.

In an implementation, an X-ray source coincides with the light source; and the third determining module is configured to determine the TOD, where $TOD=\gamma*(SID-TDD-SOSD1)$, SID represents the source to image distance, TDD represents the touch panel to detector distance, SOSD1 represents the distance between the light source and the predetermined key point, and $\gamma$ represents a correction factor.

It can be seen that, when the X-ray source coincides with the light source of the camera assembly that captures the three-dimensional image, the TOD is calculated in this implementation of the present disclosure. In addition, the correction factor is introduced, thereby improving the calculation precision.

In an implementation, an X-ray source does not coincide with the light source; and the third determining module is configured to determine a distance SOSD1 between the X-ray source and the predetermined key point based on the distance SOSD2 between the light source of the camera assembly and the predetermined key point; and determining the TOD, where $TOD=\gamma*(SID-TDD-SOSD1)$, SID represents the source to image distance, TDD represents the touch panel to detector distance, and $\gamma$ represents a correction factor.

It can be seen that when the X-ray source does not coincide with the light source of the camera assembly that captures the three-dimensional image, the TOD can be also calculated in this implementation of the present disclosure. In addition, the correction factor is introduced, thereby improving the calculation precision.

In an implementation, the third determining module is configured to determine a transformation matrix from a coordinate system of the camera assembly to a coordinate system of an X-ray generation assembly; determine three-dimensional coordinates of the predetermined key point in the coordinate system of the camera assembly based on the distance SOSD2 between the light source and the predetermined key point; determine three-dimensional coordinates of the predetermined key point in the coordinate system of the X-ray generation assembly based on the three-dimensional coordinates of the predetermined key point in the coordinate system of the camera assembly and the transformation matrix; and determine the distance SOSD1 between the X-ray source and the predetermined key point based on the three-dimensional coordinates of the predetermined key point in the coordinate system of the X-ray generation assembly.

Therefore, in this implementation of the present disclosure, the distance between the X-ray source and the predetermined key point can be conveniently determined through coordinate transformation.

In an implementation, the apparatus further includes:

a fourth determining module configured to input the three-dimensional image into a correction factor determining network corresponding to the X-ray imaging protocol, to determine the correction factor by the correction factor determining network; or determine the correction factor based on a user input.

It can be seen that, in this implementation of the present disclosure, the correction factor can be determined in various manners, and in particular, the correction factor can be determined through artificial intelligence, thereby reducing the dependence on user experience.

In an implementation, the apparatus further includes:

a training module, configured to label respective correction factors for historical three-dimensional images as training data; and train a neural network model by using the labeled historical three-dimensional images, where when an accuracy rate of an output result of the neural network model is greater than a predetermined threshold, the correction factor determining network is obtained.

Therefore, a training process for the correction factor determining network is further implemented based on the training data in this implementation of the present disclosure.

An apparatus for determining a TOD in X-ray imaging is provided, including a processor and a memory, where the memory stores an application program executable by the processor, and the application program is used to enable the processor to perform any one of the foregoing methods for determining a TOD in X-ray imaging.

It can be seen that, the implementations of the present disclosure provide an apparatus with a processor-memory architecture, and a TOD can be automatically determined based on the three-dimensional image of the to-be-detected subject without manual measurement, thereby reducing the complexity.

A computer-readable storage medium is provided, storing computer-readable instructions, the computer-readable instructions being used to perform any one of the foregoing methods for determining a TOD in X-ray imaging.

It can be seen that, the implementations of the present disclosure provide a computer-readable storage medium including computer-readable instructions, and a TOD can be automatically determined based on the three-dimensional image of the to-be-detected subject without manual measurement, thereby reducing the complexity.

6

Figure 3:
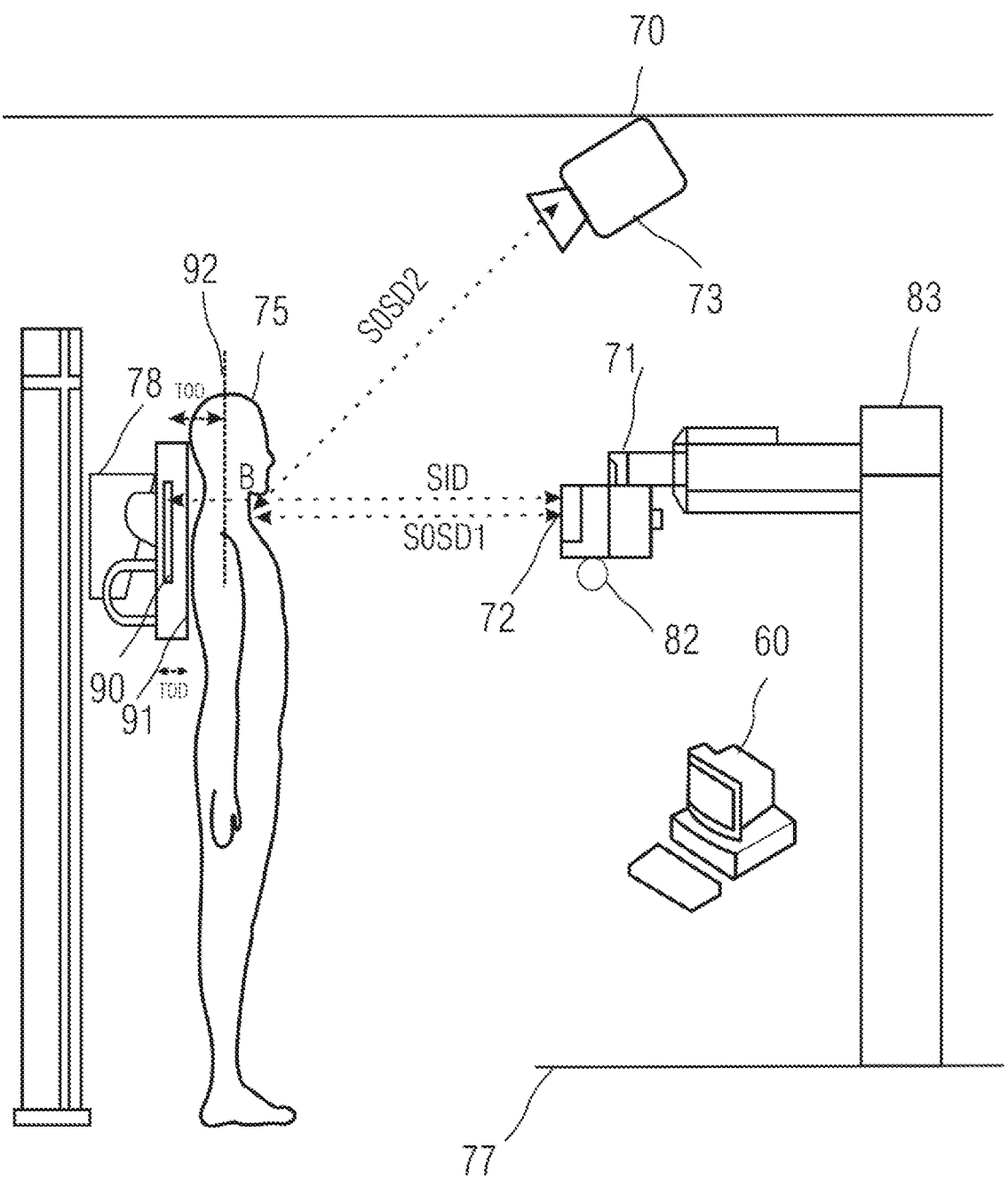
Figure 4:
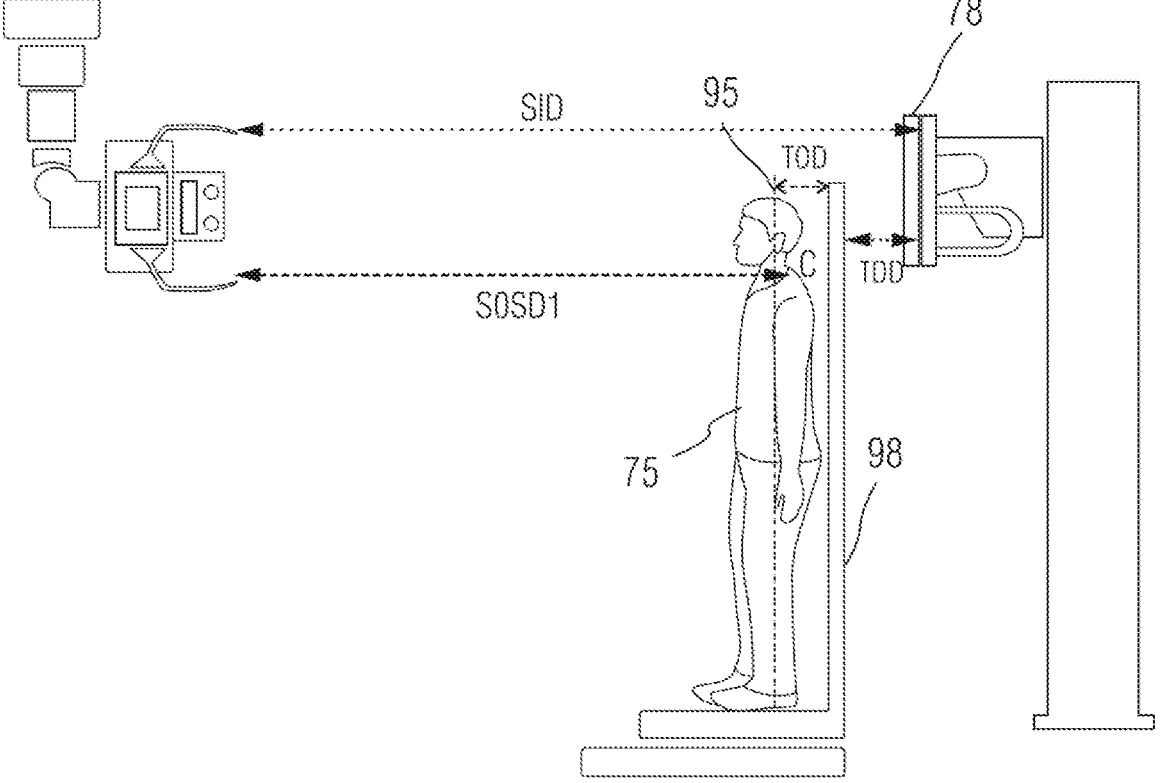
Figure 5:
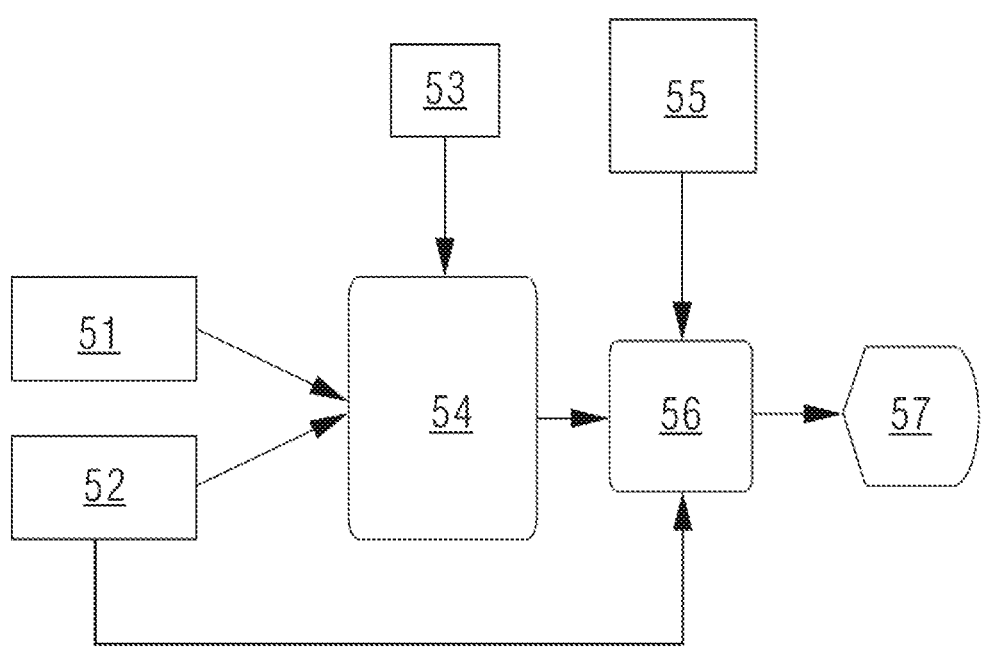
Figure 6:
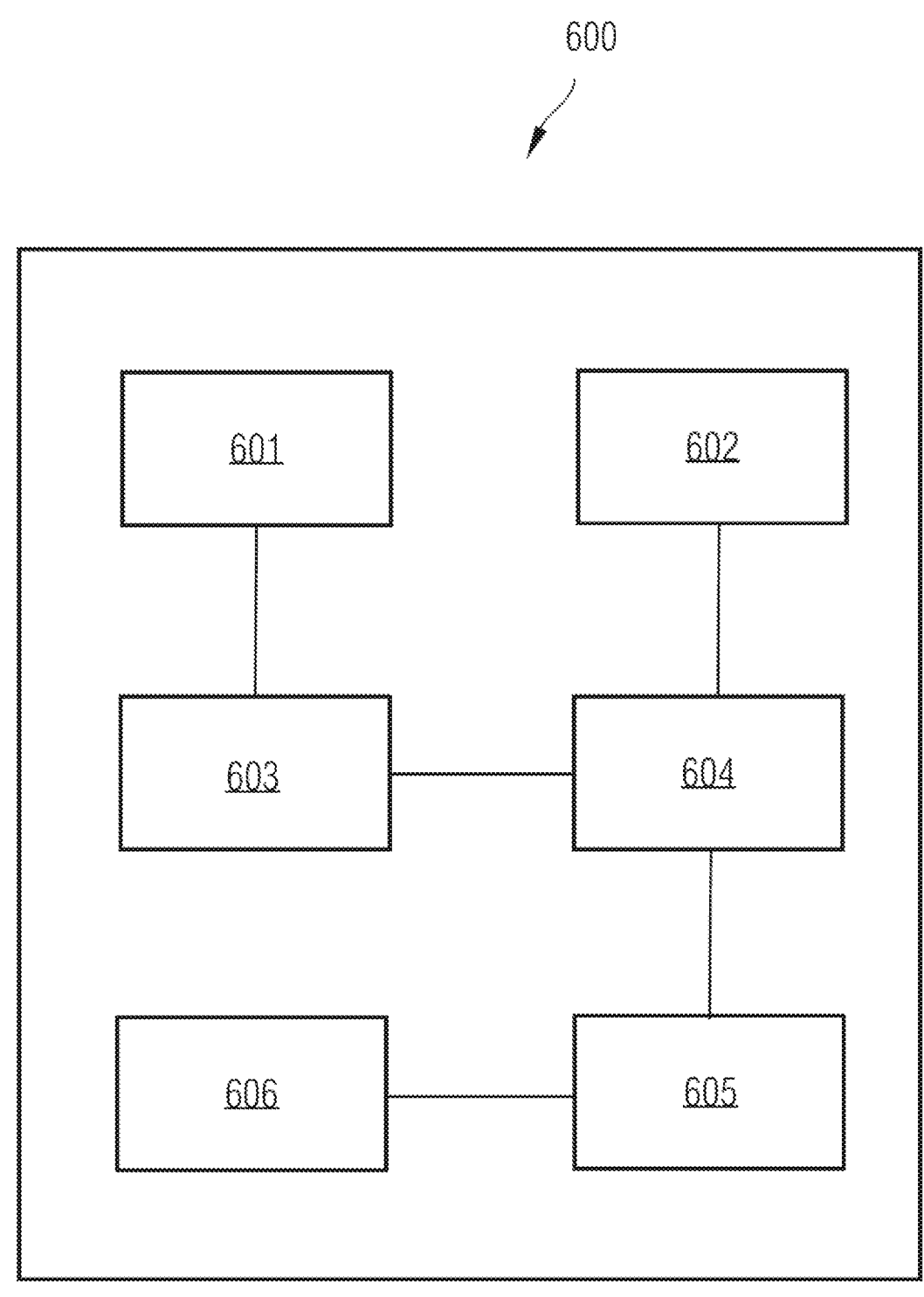
Figure 7:
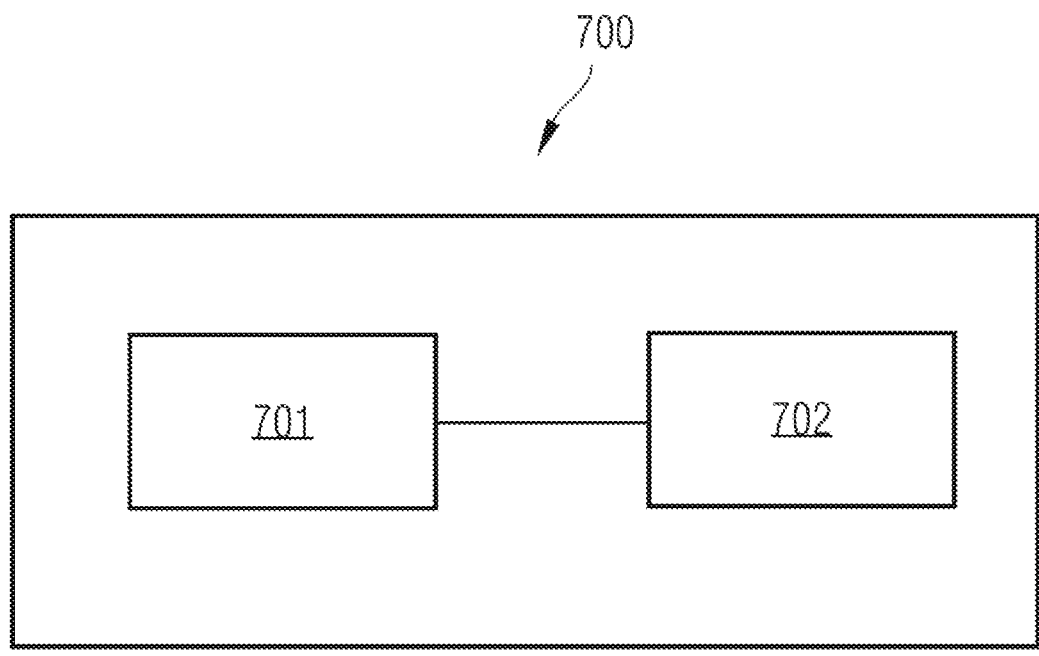

FIG. 3 illustrates a schematic diagram of an example of determining a TOD in a BWS mode (non-whole spine scan) according to an implementation of the present disclosure;

FIG. 4 illustrates a schematic diagram of an example of determining a TOD in a whole spine scan according to an implementation of the present disclosure;

FIG. 5 illustrates a schematic diagram of an example of a process of determining a TOD in X-ray imaging according to an implementation of the present disclosure;

FIG. 6 illustrates a structural diagram of an example apparatus for determining a TOD in X-ray imaging according to an implementation of the present disclosure; and FIG. 7 illustrates a structural diagram of an example apparatus that has a memory-processor architecture and is for determining a TOD in X-ray imaging according to an implementation of the present disclosure.

Reference numerals are as follows:

| 100 | Method for determining a TOD in X-ray imaging |
| 101~104 | Step |
| 70 | Ceiling |
| 71 | X-ray bulb tube |
| 72 | Beam limiting device |
| 73 | Three-dimensional camera |
| 75 | To-be-detected subject |
| 76 | Examination table assembly |
| 77 | Floor |
| 78 | Film holder assembly |
| 79 | Telescope tube sleeve |
| 81/82 | Installation position |
| 83 | Vertical column |
| 90 | Flat panel detector |
| 91 | Panel of film holder assembly |
| 92 | Neck reference line |
| 93 | Abdominal reference line |
| 95 | Spine reference line |
| 98 | Supporting plate |
| 60 | Control host |
| 51 | Two-dimensional camera |
| 52 | Depth of field sensor |
| 53 | X-ray imaging protocol |
| 54 | Correction factor determining network |
| 55 | Preset parameter |
| 56 | Arithmetic unit |
| 57 | TOD |
| 600 | Apparatus for determining a TOD |
| 601 | Obtaining module |
| 602 | First determining module |
| 603 | Second determining module |
| 604 | Third determining module |
| 605 | Fourth determining module |
| 606 | Conversion module |
| 607 | Training module |
| 700 | Apparatus for determining a TOD |
| 701 | Processor |
| 702 | Memory |

DETAILED DESCRIPTION OF THE DISCLOSURE

To make technical solutions and advantages of the present disclosure clearer and more understandable, the present disclosure is further described in detail below with reference to the accompanying drawings and implementations. It should be understood that the specific implementations described herein are merely used to illustratively explain the present disclosure but are not intended to limit the protection scope of the present disclosure.

For brief and intuitive descriptions, the following describes the solutions of the present disclosure through describing several representative implementations. A great quantity of details of the implementations are only used to help understand the solutions of the present disclosure. However, obviously, implementation of the technical solutions of the present disclosure may be not limited to such details. To avoid unnecessary ambiguousness in the solutions of the present disclosure, some implementations are not described in detail, but only a framework is given. In the following, "include" refers to "include, but is not limited to", and "according to . . . " refers to "at least according to . . . , but not limited to only according to . . . ". Because of Chinese language habits, the following does not particularly specify the quantity of a component, which means that the component may be one or more, or can be understood as at least one.

Taking into account many defects in the prior art using a ruler to manually measure a distance between a touch panel and an object included in a to-be-detected subject, the implementations of the present disclosure provide a technical solution for automatically determining a touch panel to object distance (TOD). It can be seen that, in the implementations of the present disclosure, a TOD can be automatically determined based on a three-dimensional image of a to-be-detected subject, thereby reducing the cumbersome workload in manual measurement of the TOD.

Figure 1:
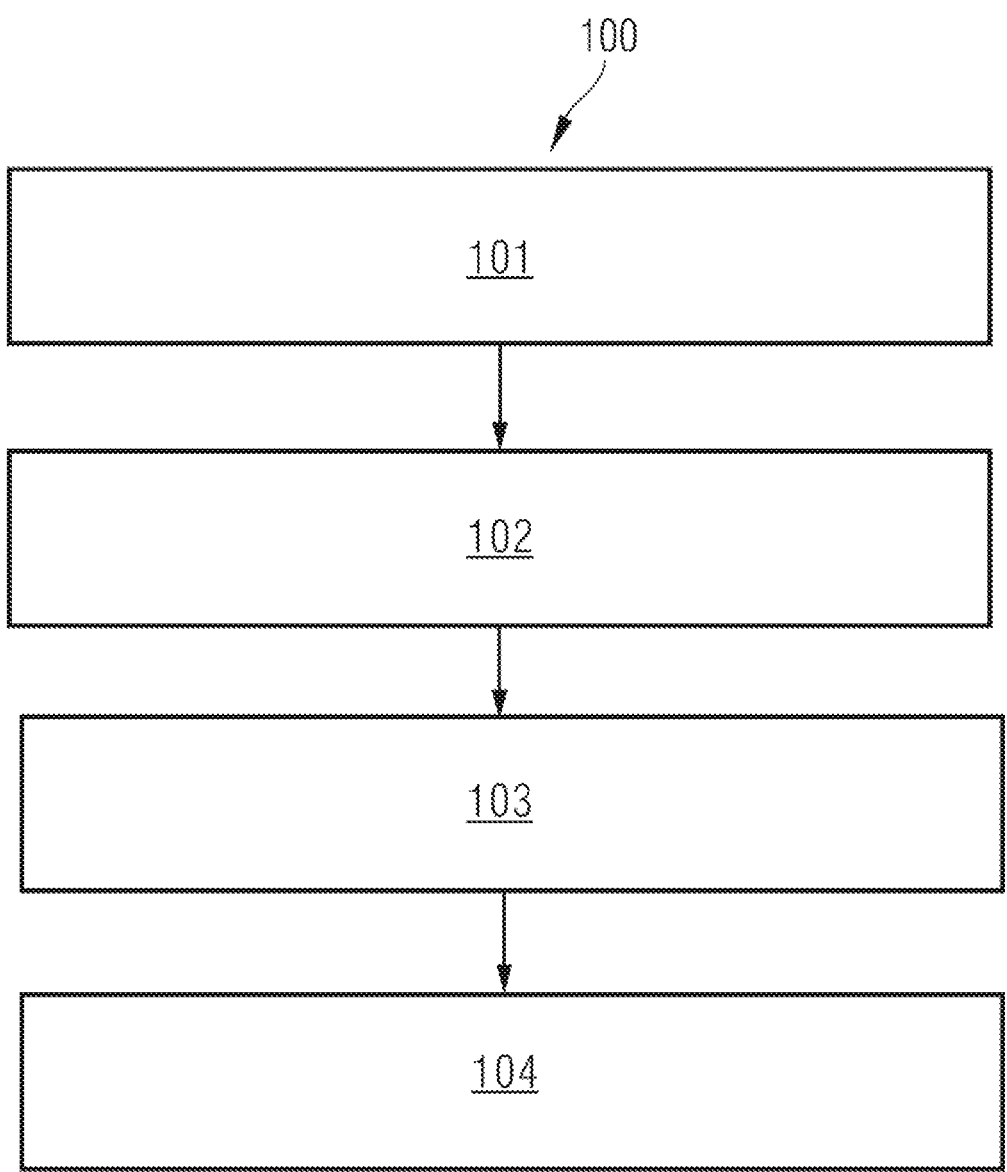
FIG. 1 illustrates a flowchart of an example method for determining a TOD in X-ray imaging according to an implementation of the present disclosure.

FIG. 1 illustrates a flowchart of a method for determining a TOD in X-ray imaging according to an implementation of the present disclosure. Preferably, the method shown in FIG. 1 may be performed by a controller. The controller may be implemented as or integrated into a control host in an X-ray imaging system, or may be implemented as a control unit independent of the control host.

As shown in FIG. 1, the method includes the following steps.

Step 101: Obtain a three-dimensional image of a to-be-detected subject that includes an object.

The to-be-detected subject is a living thing or a non-living thing on which X-ray imaging needs to be performed. The to-be-detected subject includes the object, and the object is generally located inside the to-be-detected subject. For example, when the to-be-detected subject is a living thing, the object may be tissue, an organ, a system, or the like of the living thing. The object generally corresponds to a specific X-ray imaging protocol. For example, for a whole spine scan protocol, the object is the spine of the to-be-detected subject.

In an implementation, in step 101, a camera assembly may be used to photograph the to-be-detected subject to obtain the three-dimensional image of the to-be-detected subject. In another implementation, in step 101, the three-dimensional image of the to-be-detected subject may be obtained from a storage medium (for example, a cloud or a local database). The three-dimensional image is obtained by using a camera assembly to photograph the to-be-detected subject.

Herein, a light source of the camera assembly may coincide with an X-ray source in an X-ray imaging system, or may not coincide with the X-ray source.

When the light source of the camera assembly coincides with the X-ray source in the X-ray imaging system, the camera assembly is generally fixed on an enclosure of a bulb tube or a housing of a beam limiting device of an X-ray generation assembly. For example, a groove for accommodating the camera assembly is arranged on the enclosure of the bulb tube or the housing of the beam limiting device, and the camera assembly is fixed to the groove by means of bolted connection, buckle connection, a wire rope sleeve, or the like.

When the light source of the camera assembly does not coincide with the X-ray source in the X-ray imaging system, the camera assembly may be arranged in an examination room in which the to-be-detected subject is located or at any position suitable for photographing the to-be-detected subject, for example, on the ceiling, floor, various components in a medical imaging system, or the like.

In an implementation, the camera assembly includes at least one three-dimensional camera. The three-dimensional camera photographs the to-be-detected subject by using three-dimensional imaging technologies, to generate the three-dimensional image of the to-be-detected subject.

In an implementation, the camera assembly includes at least two two-dimensional cameras. The two-dimensional cameras are respectively arranged at predetermined positions. In practice, a person skilled in the art may select suitable positions as the predetermined positions according to requirements to arrange the two-dimensional cameras. The camera assembly may further include an image processor. The image processor combines two-dimensional images captured by the two-dimensional cameras into the three-dimensional image of the to-be-detected subject. The depth of field used by the image processor in the combination may be the depth of field of any two-dimensional image. Optionally, each of the two-dimensional cameras may send a two-dimensional image captured by the two-dimensional camera to an image processor outside the camera assembly, so that the image processor outside the camera assembly can combine two-dimensional images captured by the two-dimensional cameras into the three-dimensional image of the to-be-detected subject. The depth of field used by the image processor outside the camera assembly in a combination process may also be the depth of field of any two-dimensional image. Specifically, the image processor outside the camera assembly may be implemented as a control host in the X-ray imaging system, or may be implemented as an independent control unit separate from the X-ray imaging system. Each of the two-dimensional cameras may be arranged in the examination room in which the to-be-detected subject is located or at any position suitable for photographing the to-be-detected subject, for example, on the ceiling, floor, various components in the X-ray imaging system, or the like.

In an implementation, the camera assembly may include at least one two-dimensional camera and at least one depth of field sensor. The at least one two-dimensional camera and the at least one depth of field sensor are mounted at the same position. The camera assembly may further include an image processor. The image processor generates the three-dimensional image of the to-be-detected subject by using both a depth of field provided by the depth of field sensor and a two-dimensional image provided by the two-dimensional camera. Optionally, the two-dimensional camera sends a captured two-dimensional image of the to-be-detected subject to an image processor outside the camera assembly, and the depth of field sensor sends an acquired depth of field to the image processor outside the camera assembly, so that the image processor outside the camera assembly generates the three-dimensional image of the to-be-detected subject by using both the depth of field and the two-dimensional image. Preferably, the image processor outside the camera assembly may be implemented as a control host in the X-ray imaging system, or may be implemented as an independent control unit separate from the X-ray imaging system. The two-dimensional camera may be arranged in the examination room in which the to-be-detected subject is located or at any position suitable for photographing the to-be-detected subject, for example, on the ceiling, floor, various components in a medicine imaging system, or the like.

After acquiring the three-dimensional image of the to-be-detected subject, the camera assembly may send, by using a wired interface or a wireless interface, the three-dimensional image to the controller that performs the process in FIG. 0.1. Preferably, the wired interface includes at least one of the following: a universal serial bus interface, a controller area network interface, a serial port, or the like. The wireless interface includes at least one of the following: an infrared interface, a near field communication interface, a Bluetooth interface, a ZigBee interface, a wireless broadband interface, or the like.

The foregoing exemplarily describes a typical example in which the camera assembly photographs the to-be-detected subject, to generate a three-dimensional image. A person skilled in the art may realize that the description is only exemplary and is not used to limit the protection scope of the implementations of the present disclosure.

Step 102: Determine a source to image distance (SID) and a touch panel to detector distance (TDD).

Herein, an imaging plane is a plane on which an X-ray image is formed. The imaging plane can be determined based on a position of an imaging medium in a detector. The detector is an X-ray detector and is generally a flat panel detector. A touch panel is a panel touched by the to-be-detected subject in an X-ray application. The touch panel may isolate the to-be-detected subject from an imaging plane. The touch panel generally has the following meanings:

(1). When the X-ray imaging system works in an examination table mode, the touch panel is a bed board of an examination table.

(2). When the X-ray imaging system works in a Bucky wall stand (BWS) mode under a whole spine imaging protocol, the touch panel is a supporting plate used to assist the to-be-detected subject to stand.

(3). When the X-ray imaging system works in a BWS mode under a non-whole spine imaging protocol (for example, a chest imaging protocol or a knee imaging protocol), the touch panel is a panel of a film holder assembly, and the flat panel detector is inserted into the film holder assembly.

(4). When the X-ray imaging system works in a free exposure mode (that is, the to-be-detected subject directly touches the flat panel detector), the touch panel is a panel of the flat panel detector touched by the object.

Both the SID and the TDD correspond to the X-ray imaging protocol. After the X-ray imaging protocol is determined, both the SID and the TDD are known values. Therefore, the controller that performs the process in FIG. 1 can determine the SID and the TDD based on the determined X-ray imaging protocol.

Step 103: Determine, based on the three-dimensional image, a distance between a light source of a camera assembly that captures the three-dimensional image and a predetermined key point located on a surface of the to-be-detected subject, where the predetermined key point corresponds to an X-ray imaging protocol.

Herein, the predetermined key point is a feature point that corresponds to the X-ray imaging protocol and is on the surface of the to-be-detected subject. Depending on different X-ray imaging protocols, the predetermined key point may be the left shoulder, the right shoulder, the left knee, the right knee, the left ear, the right ear, the left rump, the right rump, or the like of the to-be-detected subject. For example, when the X-ray imaging protocol is implemented as a whole spine imaging protocol, the predetermined key point may be the left shoulder or the right shoulder. When the X-ray imaging protocol is implemented as a knee imaging protocol, the predetermined key point may be the left knee or the right knee, and so on.

The predetermined key point located on the surface of the imaged to-be-detected subject in the three-dimensional image may be recognized by using a feature point extraction algorithm such as a scale-invariant feature transform (SIFT) algorithm, a speeded up robust feature (SURF) algorithm, or an oriented fast and rotated brief (ORB) algorithm. Preferably, the predetermined key point located on the surface of the to-be-detected subject in the three-dimensional image is automatically recognized through artificial intelligence, so that the artificial intelligence technologies are introduced into a medical image generation process to improve the efficiency of key point recognition.

In an implementation, step 102 specifically includes: inputting the three-dimensional image into a key point recognition network; enabling the key point recognition network to recognize the predetermined key point located on the surface of the to-be-detected subject in the three-dimensional image; and determining, based on a distance measurement algorithm (for example, various three-dimensional positioning algorithms), the distance between the light source of the camera assembly and the recognized predetermined key point.

In an implementation, the method 100 further includes a process of generating the key point recognition network. The process specifically includes the following steps: obtaining training data of the key point recognition network; and training a preset neural network model by using the training data, where when an accuracy rate of an output result of the neural network model is greater than a predetermined threshold, the key point recognition network is obtained. Specifically, the neural network model may be implemented as a feedforward neural network model, a radial basis function neural network model, a long short-term memory (LSTM) network model, an echo state network (ESN), a gate recurrent unit (GRU) network model, a deep residual network model, or the like.

The foregoing exemplarily describes a typical embodiment of a neural network model. A person skilled in the art may realize that the description is only exemplary and is not used to limit the protection scope of the implementations of the present disclosure.

Step 104: Determine the TOD based on the SID, the TDD, and the distance between the light source of the camera assembly and the predetermined key point.

In an implementation, when the X-ray source coincides with the light source of the camera assembly, step 104 specifically includes: determining the TOD, where TOD=γ* (SID−TDD−SOSD1), SID is the source to image distance, TDD is the touch panel to detector distance, SOSD1 is the distance between the light source of the camera assembly and the predetermined key point, and γ is a correction factor. In this case, because the X-ray source coincides with the light source of the camera assembly, SOSD1 is also a distance between the X-ray source and the predetermined key point.

In an implementation, when the X-ray source does not coincide with the light source of the camera assembly, step 104 specifically includes: determining a distance SOSD1 between the X-ray source and the predetermined key point based on the distance SOSD2 between the light source of the camera assembly and the predetermined key point; and determining the TOD, where TOD=$\gamma$*(SID−TDD−SOSD1), SID represents the source to image distance, TDD represents the touch panel to detector distance, and $\gamma$ represents a correction factor. Specifically, the determining a distance SOSD1 between the X-ray source and the predetermined key point based on the distance SOSD2 between the light source of the camera assembly and the predetermined key point includes: determining a transformation matrix from a coordinate system of the camera assembly to a coordinate system of an X-ray generation assembly; determining three-dimensional coordinates of the predetermined key point in the coordinate system of the camera assembly based on the distance SOSD2 between the light source of the camera assembly and the predetermined key point; determining three-dimensional coordinates of the predetermined key point in the coordinate system of the X-ray generation assembly based on the three-dimensional coordinates of the predetermined key point in the coordinate system of the camera assembly and the transformation matrix; and determining the distance SOSD1 between the X-ray source and the predetermined key point based on the three-dimensional coordinates of the predetermined key point in the coordinate system of the X-ray generation assembly.

Considering that the to-be-detected subject generally has a thickness, the TOD is further corrected by using the correction factor in this implementation of the present disclosure In an implementation, the correction factor may be provided by a user based on the experience of the user.

In another implementation, the three-dimensional image may be inputted into a correction factor determining network corresponding to the X-ray imaging protocol, to determine the correction factor by the correction factor determining network. The method 100 further includes a process of generating the correction factor determining network. The process specifically includes the following steps: labeling respective correction factors for historical three-dimensional images as training data; and training a neural network model by using the labeled historical three-dimensional images, where when an accuracy rate of an output result of the neural network model is greater than a predetermined threshold, the correction factor determining network is obtained. Specifically, the neural network model may be implemented as a feedforward neural network model, a radial basis function neural network model, an LSTM network model, an ESN, a GRU network model, a deep residual network model, or the like.

Figure 2:
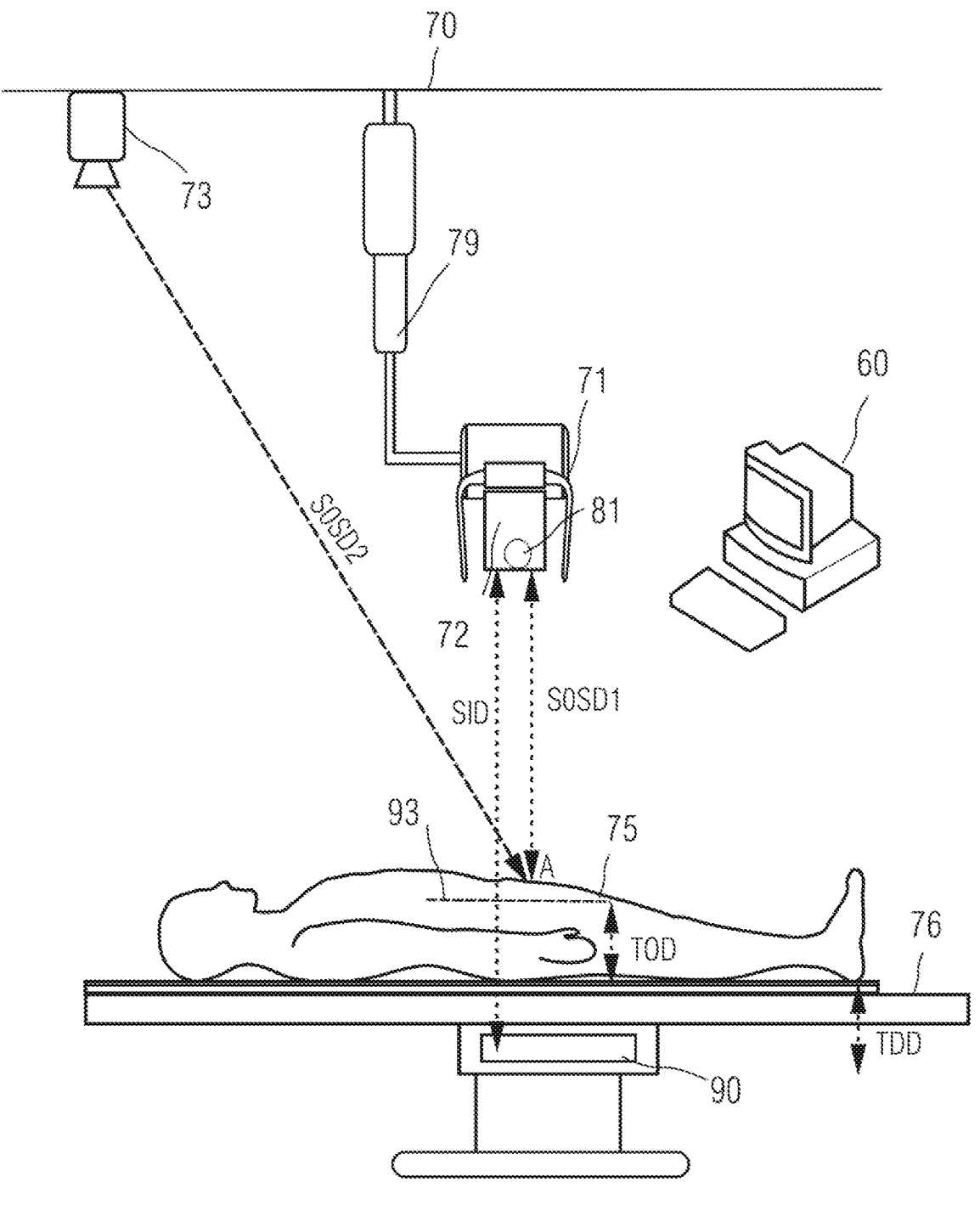
FIG. 2 illustrates a schematic diagram of an example of determining a TOD in an examination table mode according to an implementation of the present disclosure.

FIG. 2 illustrates a schematic diagram of an example of determining a TOD in an examination table mode according to an implementation of the present disclosure.

In FIG. 2, an X-ray generation assembly including an X-ray tube 71 and a beam limiting device 72 is connected to a telescope tube sleeve 79 by using a supporting piece. The telescope tube sleeve 79 is connected to a ceiling 70. Furthermore, a three-dimensional camera 73 is fixed on the ceiling 70. A photographing direction of the three-dimensional camera 73 faces towards a to-be-detected subject 75 on an examination table assembly 76. The examination table assembly 76 is further provided with a flat panel detector 90. A control host 60 may be a control host disposed in a local control room, or may be a remote control host such as a control host in a cloud.

The control host 60 includes a trained key point recognition network and a trained correction factor determining network. A training process of the key point recognition network includes: establishing an artificial neural network model; inputting labeled three-dimensional images as training data into the artificial neural network model; and training the artificial neural network model as the key point recognition network. The method for obtaining the training data for training the key point recognition network may include: first capturing a large quantity of three-dimensional images about an imaging target (for example, various people) by using a three-dimensional camera arranged at a preset position. Furthermore, experts mark the three-dimensional images to recognize key points. A training process of the correction factor determining network includes: establishing an artificial neural network model; inputting labeled three-dimensional images as training data into the artificial neural network model; and training the artificial neural network model as the correction factor determining network. The method for obtaining the training data for training the correction factor determining network may include: first capturing a large quantity of three-dimensional images about an imaging target (for example, various people) by using a three-dimensional camera arranged at a preset position. Furthermore, experts mark correction factors on the three-dimensional images based on experience.

A supervised learning manner may be used in the training processes of the correction factor determining network and the key point recognition network. Parameters of the artificial neural network model can be adjusted by using an optimization method (for example, stochastic gradient descent), so that an error between a prediction result of the artificial neural network model and a labeling result keeps decreasing until the error converges.

Assuming that an X-ray imaging protocol is an abdominal imaging protocol, the three-dimensional camera 73 photographs the to-be-detected subject 75 to acquire a three-dimensional image of the to-be-detected subject 75. The three-dimensional camera 73 sends the three-dimensional image of the to-be-detected subject 75 to the control host 60 through wired or wireless communication with the control host 60. The control host 60 determines that a predetermined key point corresponding to the abdominal imaging protocol is the belly button.

The key point recognition network in the control host 60 recognizes a belly button point A located on a surface of the to-be-detected subject 75 in the three-dimensional image of the to-be-detected subject 75. The control host 60 determines a distance SOSD2 between a light source of the three-dimensional camera 73 and the recognized belly button point A by using a distance measurement algorithm, and determines three-dimensional coordinates of the belly button point A in a coordinate system of the three-dimensional camera 73 based on the SOSD2. The control host 60 determines three-dimensional coordinates of the belly button point A in a coordinate system of the X-ray generation assembly based on the three-dimensional coordinates of the belly button point A in the coordinate system of the three-dimensional camera 73 and based on a transformation matrix between the coordinate system of the three-dimensional camera 73 and the coordinate system of the X-ray generation assembly. The control host 60 then determines a distance SOSD1 between the X-ray source and the belly button point A by using the three-dimensional coordinates of the belly button point A in the coordinate system of the X-ray generation assembly.

The control host 60 stores preset parameters of the abdominal imaging protocol. The preset parameters include a SID and a TDD. Herein, a distance between the X-ray source and an imaging plane of the flat panel detector 90 is the SID, and a distance between an examination table assembly 76 and the flat panel detector 90 is the TDD. The correction factor determining network in the control host 60 determines a correction factor γ of the three-dimensional image of the to-be-detected subject 75. A TOD is a distance between an abdominal reference line 93 (that is, the object) of the to-be-detected subject 75 and the examination table assembly 76 (that is, the touch panel). The control host 60 calculates the TOD, where TOD=γ*(SID−TDD−SOSD1).

The three-dimensional camera 73 may be not arranged on the ceiling 70. For example, the three-dimensional camera 73 may be arranged at an installation position 81 on a housing of the beam limiting device 72, to help the X-ray source coincide with the light source of the three-dimensional camera 73.

When the X-ray source coincides with the light source of the three-dimensional camera 73, the control host 60 calculates the TOD, where TOD=γ*(SID−TDD−SOSD1). In this case, the control host 60 determines the distance SOSD1 between the light source of the three-dimensional camera 73 and the recognized belly button point A by using the distance measurement algorithm. SOSD1 is also the distance between the X-ray source and the belly button point A.

FIG. 3 illustrates a schematic diagram of an example of determining a TOD in a BWS mode (non-whole spine scan) according to an implementation of the present disclosure.

In FIG. 3, an X-ray generation assembly including an X-ray tube 71 and a beam limiting device 72 is connected, by using a supporting piece, to a vertical column 83 arranged on a floor 77. A to-be-detected subject 75 stands near a film holder assembly 78. Furthermore, a three-dimensional camera 73 is fixed on a ceiling 70. A photographing direction of the three-dimensional camera 73 faces towards the to-be-detected subject 75 near the film holder assembly 78. The film holder assembly 78 is further provided with a flat panel detector 90.

A control host 60 may be a control host disposed in a local control room, or may be a remote control host such as a control host in a cloud.

The control host 60 includes a trained key point recognition network and a trained correction factor determining network. A training process of the key point recognition network includes: establishing an artificial neural network model; inputting labeled three-dimensional images as training data into the artificial neural network model; and training the artificial neural network model as the key point recognition network. The method for obtaining the training data for training the key point recognition network may include: first capturing a large quantity of three-dimensional images about an imaging target (for example, various people) by using a three-dimensional camera arranged at a preset position. Furthermore, experts mark the three-dimensional images to recognize key points. A training process of the correction factor determining network includes: establishing an artificial neural network model; inputting labeled three-dimensional images as training data into the artificial neural network model; and training the artificial neural network model as the correction factor determining network. The method for obtaining the training data for training the correction factor determining network may include: first capturing a large quantity of three-dimensional images about an imaging target (for example, various people) by using a three-dimensional camera arranged at a preset position. Furthermore, experts mark correction factors on the three-dimensional images based on experience.

A supervised learning manner may be used in the training processes of the correction factor determining network and the key point recognition network. Parameters of the artificial neural network model can be adjusted by using an optimization method (for example, stochastic gradient descent), so that an error between a prediction result of the artificial neural network model and a labeling result keeps decreasing until the error converges.

Assuming that an X-ray imaging protocol is a neck imaging protocol, the three-dimensional camera 73 photographs the to-be-detected subject 75 to acquire a three-dimensional image of the to-be-detected subject 75. The three-dimensional camera 73 sends the three-dimensional image of the to-be-detected subject 75 to the control host 60 through wired or wireless communication with the control host 60. The control host 60 determines that a predetermined key point corresponding to the neck imaging protocol is a laryngeal prominence point.

The key point recognition network in the control host 60 recognizes a laryngeal prominence point B located on a surface of the to-be-detected subject 75 in the three-dimensional image of the to-be-detected subject 75. The control host 60 determines a distance SOSD2 between a light source of the three-dimensional camera 73 and the recognized laryngeal prominence point B by using a distance measurement algorithm, and determines three-dimensional coordinates of the laryngeal prominence point B in a coordinate system of the three-dimensional camera 73 based on the SOSD2. The control host 60 determines three-dimensional coordinates of the laryngeal prominence point B in a coordinate system of the X-ray generation assembly based on the three-dimensional coordinates of the laryngeal prominence point B in the coordinate system of the three-dimensional camera 73 and based on a transformation matrix between the coordinate system of the three-dimensional camera 73 and the coordinate system of the X-ray generation assembly. The control host 60 then determines a distance SOSD1 between the X-ray source and the laryngeal prominence point B by using the three-dimensional coordinates of the laryngeal prominence point B in the coordinate system of the X-ray generation assembly.

The control host 60 stores preset parameters of the neck imaging protocol. The preset parameters include a SID and a TDD. Herein, a distance between the X-ray source and an imaging plane of the flat panel detector 90 is the SID, and a distance between a panel 91 (that is, the touch panel) of the film holder assembly 78 and the flat panel detector 90 in the film holder assembly 78 is the TDD. The correction factor determining network in the control host 60 determines a correction factor γ of the three-dimensional image of the to-be-detected subject 75. A TOD is a distance between a neck reference line 92 (that is, the object) of the to-be-detected subject 75 and the panel 91 of the film holder assembly 78. The control host 60 calculates the TOD, where TOD=γ*(SID−TDD−SOSD1).

The three-dimensional camera 73 may be not arranged on the ceiling 70. For example, the three-dimensional camera 73 may be arranged at an installation position 82 on a housing of the beam limiting device 72, to help the X-ray source coincide with the light source of the three-dimensional camera 73. When the X-ray source coincides with the light source of the three-dimensional camera 73, the control host 60 calculates the TOD, where TOD=γ*(SID−TDD−SOSD1). In this case, the control host 60 determines the distance SOSD1 between the light source of the three-dimensional camera 73 and the recognized laryngeal prominence point B by using the distance measurement algorithm. SOSD1 is also the distance between the X-ray source and the laryngeal prominence point B.

In a BWS mode during non-whole spine imaging, the to-be-detected subject approaches the film holder assembly 78. The difference lies in that, in a BWS mode during whole spine imaging, the to-be-detected subject does not directly approach the film holder assembly 78, but stands on a supporting plate 98.

FIG. 4 illustrates a schematic diagram of an example of determining a TOD in a whole spine scan according to an implementation of the present disclosure.

It can be seen that a to-be-detected subject 75 stands on a supporting plate 98. A predetermined key point corresponding to the whole spine scan is a shoulder C (the left shoulder or the right shoulder). A distance between an X-ray source and an imaging plane of a flat panel detector in a film holder assembly 78 is a SID. A distance between the supporting plate 98 and the flat panel detector in the film holder assembly 78 is a TDD. A distance between a spine reference line 95 and the supporting plate 98 is a TOD.

FIG. 5 illustrates a schematic diagram of an example of a process of determining a TOD in X-ray imaging according to an implementation of the present disclosure.

As shown in FIG. 5, the process includes the following steps. A two-dimensional camera 51 captures a two-dimensional image of a to-be-detected subject that includes an object. A depth of field sensor 52 obtains depth-of-field information of the to-be-detected subject. A correction factor determining network 54 in a control host generates a three-dimensional image based on the two-dimensional image and the depth-of-field information, and determines a correction factor of the three-dimensional image corresponding to an X-ray imaging protocol 53. An arithmetic unit 56 in the control host receives preset parameters 55 (including a SID and a TDD) corresponding to the X-ray imaging protocol 53, determines a distance between a light source of a camera assembly and a predetermined key point located on a surface of the to-be-detected subject based on the three-dimensional image, and calculates a TOD 57 based on the correction factor, the SID, the TDD, and the distance between the light source of the camera assembly and the predetermined key point located on the surface of the to-be-detected subject.

Based on the foregoing descriptions, the implementations of the present disclosure further provide an apparatus for determining a TOD in X-ray imaging. FIG. 6 illustrates a structural diagram of an apparatus for determining a TOD in X-ray imaging according to an implementation of the present disclosure.

As shown in FIG. 6, an apparatus 600 includes:

an obtaining module 601, configured to obtain a three-dimensional image of a to-be-detected subject that includes an object;

a first determining module 602, configured to determine a SID and a TDD;

a second determining module 603, configured to determine, based on the three-dimensional image, a distance between a light source of a camera assembly that captures the three-dimensional image and a predetermined key point located on a surface of the to-be-detected subject, where the predetermined key point corresponds to an X-ray imaging protocol; and a third determining module 604, configured to determine the TOD based on the SID, the TDD, and the distance between the light source of the camera assembly and the predetermined key point.

In an implementation, the second determining module 603 is configured to input the three-dimensional image into a key point recognition network; enable the key point recognition network to recognize the predetermined key point located on the surface of the to-be-detected subject in the three-dimensional image; and determine, based on a distance measurement algorithm, the distance between the light source of the camera assembly and the recognized predetermined key point.

In an implementation, an X-ray source coincides with the light source of the camera assembly that captures the three-dimensional image. The third determining module 604 is configured to determine the TOD, where TOD=$\gamma$*(SID−TDD−SOSD1), SID is the source to image distance, TDD is the touch panel to detector distance, SOSD1 is the distance between the light source of the camera assembly and the predetermined key point, and $\gamma$ is a correction factor.

In an implementation, an X-ray source does not coincide with the light source of the camera assembly that captures the three-dimensional image. The third determining module 604 is configured to determine a distance SOSD1 between the X-ray source and the predetermined key point based on the distance SOSD2 between the light source of the camera assembly and the predetermined key point; and determine the TOD, where TOD=$\gamma$*(SID−TDD−SOSD1), SID is the source to image distance, TDD is the touch panel to detector distance, and $\gamma$ is a correction factor.

In an implementation, the third determining module 604 is configured to determine a transformation matrix from a coordinate system of the camera assembly to a coordinate system of an X-ray generation assembly; determine three-dimensional coordinates of the predetermined key point in the coordinate system of the camera assembly based on the distance SOSD2 between the light source of the camera assembly and the predetermined key point; determine three-dimensional coordinates of the predetermined key point in the coordinate system of the X-ray generation assembly based on the three-dimensional coordinates of the predetermined key point in the coordinate system of the camera assembly and the transformation matrix; and determine the distance SOSD1 between the X-ray source and the predetermined key point based on the three-dimensional coordinates of the predetermined key point in the coordinate system of the X-ray generation assembly.

In an implementation, a fourth determining module 605 is further included and configured to input the three-dimensional image into a correction factor determining network corresponding to the X-ray imaging protocol, to determine the correction factor by the correction factor determining network; or determine the correction factor based on a user input.

In an implementation, a training module 606 is further included and configured to label respective correction factors for historical three-dimensional images as training data; and train a neural network model by using the labeled historical three-dimensional images, where when an accuracy rate of an output result of the neural network model is greater than a predetermined threshold, the correction factor determining network is obtained.

FIG. 7 illustrates a structural diagram of an apparatus that has a memory-processor architecture and is for determining a TOD in X-ray imaging according to an implementation of the present disclosure.

As shown in FIG. 7, an apparatus 700 for determining a TOD in X-ray imaging includes a processor 701, a memory 702, and a computer program stored on the memory 702 and executable on the processor 701. The computer program, when executed by the processor 701, implements any one of the foregoing methods for determining a TOD in X-ray imaging. The memory 702 may be specifically implemented as various storage media such as an electrically erasable programmable read-only memory (EEPROM), a flash memory, and a programmable read-only memory (PROM).

The processor 701 may be implemented to include one or more central processing units (CPUs) or implemented as one or more field programmable gate arrays. The field programmable gate array integrates one or more CPU cores. Specifically, the CPU or the CPU core may be implemented as a CPU, a microcontroller unit (MCU), a digital signal processor (DSP), or the like.

It should be noted that not all steps and modules in the procedures and the structural diagrams are necessary, and some steps or modules may be omitted according to an actual requirement. An execution sequence of the steps is not fixed and may be adjusted according to needs. Division of the modules is merely functional division for ease of description. During actual implementation, one module may be implemented separately by a plurality of modules, and functions of the plurality of modules may alternatively be implemented by the same module. The modules may be located in the same device or in different devices.

Hardware modules in the implementations may be implemented in a mechanical manner or an electronic manner. For example, a hardware module may include specially designed permanent circuits or logic devices (for example, an application specific processor such as an FPGA or an ASIC) to complete specific operations. The hardware module may also include temporarily configured programmable logic devices or circuits (for example, including a universal processor or another programmable processor) to perform specific operations. The hardware module is implemented by specifically using the mechanical manner, using the application-specific permanent circuits, or using the temporarily configured circuits (for example, configured by software), which can be decided according to consideration of costs and time.

The present disclosure further provides a machine-readable storage medium, which stores instructions that are used to make a machine to execute the instructions of the method described in this specification. Specifically, a system or an apparatus that is equipped with a storage medium may be provided. The storage medium stores software program code that implements functions of any implementation in the foregoing embodiments, and a computer (a CPU or an MPU) of the system or the apparatus is enabled to read and execute the program code stored in the storage medium. In addition, a program code based instruction may also be used to enable an operating system or the like running in the computer to complete some or all actual operations. The program code read from the storage medium may also be written into a memory that is disposed in an expansion board inserted in the computer, or may be written into a memory that is disposed in an expansion unit connected to the computer, and then a CPU or the like that is installed on the expansion board or expansion unit may be enabled to execute some or all actual operations based on the instructions of the program code, so as to implement the functions of any one of the foregoing implementations. Implementations of the storage medium for providing the program code may include a floppy disk, a hard disk, a magneto-optical disk, an optical memory (such as a CD-ROM, a CD-R, a CD-RW, a DVD-ROM, a DVD-RAM, a DVD-RW, and a DVD+RW), a magnetic tape, a non-volatile storage card, and a ROM. Optionally, the program code may be downloaded from a server computer or a cloud by using a communication network.

The foregoing descriptions are merely preferred implementations of the present disclosure, and are not intended to limit the protection scope of the present disclosure. Any modification, equivalent replacement, or improvement made within the spirit and principle of the present disclosure shall fall within the protection scope of the present disclosure.

The various components described herein may be referred to as "units" or "modules." Such components may be implemented via any suitable combination of hardware and/or software components as applicable and/or known to achieve their intended respective functionality. This may include mechanical and/or electrical components, processors, processing circuitry, or other suitable hardware components, in addition to or instead of those discussed herein. Such components may be configured to operate independently, or configured to execute instructions or computer programs that are stored on a suitable computer-readable medium. Regardless of the particular implementation, such units and/or modules, as applicable and relevant, may alternatively be referred to herein as "circuitry," "controllers," "processors," or "processing circuitry," or alternatively as noted herein.

What is claimed is:

1. A method for determining a touch panel to object distance (TOD) in X-ray imaging, comprising:
   obtaining a three-dimensional image of a to-be-detected subject that comprises an object;
   determining a source to image distance (SID) and a touch panel to detector distance (TDD);
   determining, based on the three-dimensional image, a distance between a light source of a camera assembly that captures the three-dimensional image and a predetermined point located on a surface of the to-be-detected subject;
   and
   determining the TOD based on the SID, the TDD, and the distance between the light source and the predetermined point by evaluating:
   TOD=$\gamma$*(SID−TDD−SOSD1), wherein:
      the predetermined point corresponds to an X-ray imaging protocol,
      the light source is not part of an X-ray source used for the X-ray imaging,
      the distance SOSD1 is determined between the X-ray source and the predetermined point based on a distance SOSD2 between the light source of the camera assembly and the predetermined point,
      SID represents the source to image distance,
      TDD represents the touch panel to detector distance, and
      $\gamma$ represents a correction factor.

2. The method according to claim 1, wherein the determining the distance between the light source and the predetermined point located on the surface of the to-be-detected subject comprises:
   inputting the three-dimensional image into a point recognition network;
   enabling the point recognition network to recognize the predetermined point located on the surface of the to-be-detected subject in the three-dimensional image; and
   determining, based on a distance measurement algorithm, a distance between the light source and a recognized predetermined point.

3. The method according to claim 1, wherein the determining the distance SOSD1 between the X-ray source and the predetermined point comprises:
   determining a transformation matrix from a coordinate system of the camera assembly to a coordinate system of an X-ray generation assembly;

determining three-dimensional coordinates of the predetermined point in the coordinate system of the camera assembly based on the distance SOSD2 between the light source and the predetermined point;

determining three-dimensional coordinates of the predetermined point in the coordinate system of the X-ray generation assembly based on the three-dimensional coordinates of the predetermined point in the coordinate system of the camera assembly and the transformation matrix; and determining the distance SOSD1 between the X-ray source and the predetermined point based on the three-dimensional coordinates of the predetermined point in the coordinate system of the X-ray generation assembly.

4. The method according to claim 1, further comprising:

determining the correction factor by inputting the three-dimensional image into a correction factor determining network corresponding to the X-ray imaging protocol.

5. The method according to claim 1, further comprising:

determining the correction factor based upon a user input.

6. The method according to claim 4, further comprising:

labeling respective correction factors for historical three-dimensional images as training data;

training a neural network model by using labeled historical three-dimensional images; and generating the correction factor determining network when an accuracy rate of an output result of the neural network model is greater than a predetermined threshold.

7. An apparatus for determining a touch panel to object distance (TOD) in X-ray imaging, comprising:

obtaining processing circuitry configured to obtain a three-dimensional image of a to-be-detected subject that comprises an object;

first determining processing circuitry configured to determine a source to image distance (SID) and a touch panel to detector distance (TDD);

second determining processing circuitry configured to determine, based on the three-dimensional image, a distance between a light source of a camera assembly that captures the three-dimensional image and a predetermined point located on a surface of the to-be-detected subject; and third determining processing circuitry configured to determine the TOD based on the SID, the TDD, and the distance between the light source and the predetermined point by evaluating:

TOD=$\gamma$*(SID−TDD−SOSD1), wherein:

the predetermined point corresponds to an X-ray imagine protocol, the light source is not part of an X-ray source used for the X-ray imaging, the distance SOSD1 between the X-ray source and the predetermined point is determined based on a distance SOSD2 between the light source of the camera assembly and the predetermined point, SID represents the source to image distance, TDD represents the touch panel to detector distance, and $\gamma$ represents a correction factor.

8. The apparatus according to claim 7, wherein the second determining processing circuitry is configured to:

input the three-dimensional image into a point recognition network;

enable the point recognition network to recognize the predetermined point located on the surface of the to-be-detected subject in the three-dimensional image; and determine, based on a distance measurement algorithm, a distance between the light source and a recognized predetermined point.

9. The apparatus according to claim 7, wherein the third determining processing circuitry is configured to:

determine a transformation matrix from a coordinate system of the camera assembly to a coordinate system of an X-ray generation assembly;

determine three-dimensional coordinates of the predetermined point in the coordinate system of the camera assembly based on the distance SOSD2 between the light source and the predetermined point;

determine three-dimensional coordinates of the predetermined point in the coordinate system of the X-ray generation assembly based on the three-dimensional coordinates of the predetermined point in the coordinate system of the camera assembly and the transformation matrix; and determine the distance SOSD1 between the X-ray source and the predetermined point based on the three-dimensional coordinates of the predetermined point in the coordinate system of the X-ray generation assembly.

10. The apparatus according to claim 1, further comprising:

fourth determining processing circuitry configured to determine the correction factor by inputting the three-dimensional image into a correction factor determining network corresponding to the X-ray imaging protocol.

11. The apparatus according to claim 10, further comprising:

fourth determining processing circuitry configured to determine the correction factor the based upon a user input.

12. The apparatus according to claim 10, further comprising:

training processing circuitry configured to:

label respective correction factors for historical three-dimensional images as training data;

train a neural network model by using labeled historical three-dimensional images; and generate the correction factor determining network when an accuracy rate of an output result of the neural network model is greater than a predetermined threshold.

13. A non-transitory computer-readable storage medium having instructions stored thereon that, when executed by a processor, cause the processor to determine a touch panel to object distance (TOD) in X-ray imaging by:

obtaining a three-dimensional image of a to-be-detected subject that comprises an object;

determining a source to image distance (SID) and a touch panel to detector distance (TDD);

determining, based on the three-dimensional image, a distance between a light source of a camera assembly that captures the three-dimensional image and a predetermined point located on a surface of the to-be-detected subject;

determining the TOD based on the SID, the TDD, and the distance between the light source and the predetermined point by evaluating;

TOD=$\gamma$*(SID−TDD−SOSD1), wherein;

the predetermined point corresponds to an X-ray imagine protocol the light source is not part of an X-ray source used for the X-ray imaging, the distance SOSDI between the X-ray source and the predetermined point is determined based on a distance SOSD2 between the light source of the camera assembly and the predetermined point, SID represents the source to image distance, TDD represents the touch panel to detector distance, and γ represents a correction factor.

$*$   $*$   $*$   $*$   $*$